US010258665B2

(12) United States Patent
Aronow et al.

(10) Patent No.: US 10,258,665 B2
(45) Date of Patent: *Apr. 16, 2019

(54) METHODS AND DEVICES FOR BONE INFECTION TREATMENT SELECTION

(71) Applicant: Children's Hospital Medical Center, Cincinnati, OH (US)

(72) Inventors: Bruce J. Aronow, Cincinnati, OH (US); John B. Harley, Cincinnati, OH (US); Margaret Hostetter, Cincinnati, OH (US); Kenneth Kaufman, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/978,332

(22) Filed: May 14, 2018

(65) Prior Publication Data

US 2018/0256676 A1 Sep. 13, 2018

Related U.S. Application Data

(63) Continuation of application No. 14/681,673, filed on Apr. 8, 2015, now Pat. No. 9,999,652.

(60) Provisional application No. 61/978,614, filed on Apr. 11, 2014.

(51) Int. Cl.
*C12Q 1/6883* (2018.01)
*A61K 38/14* (2006.01)
*A61K 31/7036* (2006.01)

(52) U.S. Cl.
CPC .......... *A61K 38/14* (2013.01); *A61K 31/7036* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS 9,999,652 B2  6/2018  Aronow et al.
2003/0092019 A1  5/2003  Meyer et al.

OTHER PUBLICATIONS

Hegele (Arterioscler Throm Vasc Biol 2002 vol. 22 pp. 1058-1061).*
Lucentini (The Scientist 2004 vol. 18 pp. 1-3).*
Alberts, B., et al., "Studying Gene Expression and Function," Molecular Biology of the Cell, 4th Ed., Garland Science, 2002, 18 pgs.
Ardura MI, et al., "Enhanced monocyte response and decreased central memory T cells in children with invasive *Staphylococcus aureus* infections," PLoS One, 2009; 4(5):e5446, 17 pgs.
Becamel C, et al., "Interaction of serotonin 5-hydroxytryptamine type 2C receptors with PDZ10 of the multi-PDZ domain protein MUPP1," J Biol Chem, 2001; 276(16):12974-82, 10 pgs.
Bill BR, et al., "A primer for morpholino use in zebrafish," Zebrafish, 2009; 6(1):69-77, 16 pgs.
Collins MM, et al., "*Claudin*-5 expression in the vasculature of the developing chick embryo," Gene expression patterns, 2012, 12:123-129, 7 pgs.
Dinauer MC., "Chronic granulomatous disease and other disorders of phagocyte function," Hematology Am Soc Hematol Educ Program, 2005, p. 89-95, 7 pgs.
Frank CF, et al., "Cleavage of E-cadherin: a mechanism for disruption of the intestinal epithelial barrier by *Candida albicans*," Translational research: The Journal of Laboratory and Clinical Medicine, 2007; 149(4):211-22, 12 pgs.
Frieden, M. et al., "Locked Nucleic Acid Holds Promise in the Treatment of Cancer," Curr Pharm Des, 2008, 14(11):1138-1142, Abstract Only, 1 pg.
Furuse M, et al., "The role of claudin-based tight junctions in morphogenesis," Annals of the New York Academy of Sciences, 2009; 1165:58-61, 4 pgs.
Gordon DL, et al., "Ligand-receptor interactions in the phagocytosis of virulent *Streptococcus pneumoniae* by polymorphonuclear leukocytes," J Infect Dis 1986; 154(4):619-26, 8 pgs.
Guillemot L, et al., "Paracingulin regulates the activity of Rac1 and RhoA GTPases by recruiting Tiam1 and GEF-H1 to epithelial junctions," Molecular Biology of the Cell, 2008; 19(10):4442-53, 12 pgs.
Hegele, R.A., "SNP Judgments and Freedom of Association," Arterioscler Thromb Vasc Biol, 2002, 22:1058-1061, 5 pgs.
Holland SM, et al., "STAT3 mutations in the hyper-IgE syndrome," N Engl J Med, 2007; 357(16):1608-19, 12 pgs.
Hoskins EE, et al., "Fanconi anemia deficiency stimulates HPV-associated hyperplastic growth in organotypic epithelial raft culture," Oncogene, 2009; 28(5):674-85, 12 pgs.
Ku CL, et al., "*IRAK4* and *NEMO* mutations in otherwise healthy children with recurrent invasive pneumococcal disease," J Med Genet, 2007; 44(1):16-23, 8 pgs.
Kwong RW, et al., "The tight junction protein claudin-b regulates epithelial permeability and sodium handling in larval zebrafish, *Danio rerio*," American Journal of Physiology Regulatory, Integrative and Comparative Physiology, 2013; 304(7):R504-13, 10 pgs.
Lanaspa MA, et al., "The tight junction protein, MUPP1, is upregulated by hypertonicity and is important in the osmotic stress response in kidney cells," Proceedings of the National Academy of Sciences of the United States of America 2007; 104(34):13672-7, 6 pgs.

(Continued)

*Primary Examiner* — Amanda Haney
(74) *Attorney, Agent, or Firm* — Frost Brown Todd LLC

(57) ABSTRACT

Disclosed are methods for identifying patients at increased risk of developing disseminated staphylococcal infection, which includes the steps of determining that the patient has a mutation in one or more genes selected from a MPDZ network gene, a CGNL1 network gene, a PRKRIR network gene, a MED26 network gene, a tight junction protein gene, or an immune modulator gene; and treating the patient for disseminated staphylococcal infection. Also disclosed are solid substrates and/or assays useful for carrying out the disclosed methods.

5 Claims, No Drawings

(56) References Cited

OTHER PUBLICATIONS

Le Saux N, et al., "Shorter courses of parenteral antibiotic therapy do not appear to influence response rates for children with acute hematogenous osteomyelitis: a systematic review," BMC Infectious Diseases, 2002; 2:16, 9 pgs.

Liu, C., et al., "Clinical Practice Guidelines by the Infectious Diseases Society of America for the Treatment of Methicillin-Resistant *Staphylococcus aureus* Infections in Adults and Children," Clinical Infectious Diseases Advance Access, Jan. 2011, CID, 2011:52, 38 pgs.

Lucentini, J., "Gene Association Studies Typically Wrong: Reproducible gene-disease associations are few and far between," The Scientist, Dec. 2004, 18(24):20, 6 pgs.

Montes, A.H., et al., "A Functional Polymorphism in *MMP1* Could Influence Osteomyelitis Development," Journal of Bone and Mineral Research, Apr. 2010, 25(4):912-919, 8 pgs.

Mummidi, S., et al., "Evolution of Human and Non-human Primate CC Chemokine Receptor 5 Gene and mRNA," The Journal of Biological Chemistry, Jun. 2000, 275(25):18946-18961, 16 pgs.

Nehme, N.T., et al., "MST1 mutations in autosomal recessive primary immunodeficiency characterized by defective naïve T-cell survival," Blood, Apr. 2012, 119(15):3458-3468, 12 pgs.

Nelson PT, et al., "Microarray-based, high-throughput gene expression profiling of microRNAs," Nature Methods, 2004, 1(2):155-161, 8 pgs.

Nelson PT, et al., "RAKE and LNA-ISH reveal microRNA expression and localization in archival human brain," RNA, 2006, 12(2):187-191, 6 pgs.

Ohnishi H, et al., "JACOP, a Novel Plaque Protein Localizing at the Apical Junctional Complex with Sequence Similarity to Cingulin," J Biol Chem, 2004; 279(44):46014-22, 10 pgs.

Paschoud S, et al., "Distinct domains of paracingulin are involved in its targeting to the actin cytoskeleton and regulation of apical junction assembly," J Biol Chem, 2012; 287(16):13159-69, 17 pgs.

Paschoud S, et al., "Cingulin and paracingulin show similar dynamic behaviour, but are recruited independently to junctions," Molecular Membrane Biology 2011; 28(2):123-35, 22 pgs.

Prodromou C, et al., "Structural basis of the radicicol resistance displayed by a fungal hsp90," ACS Chemical Biology, 2009; 4(4):289-97, 9 pgs.

Pulimeno P, et al., "A role for ZO-1 and PLEKHA7 in recruiting paracingulin to tight and adherens junctions of epithelial cells," J Biol Chem, 2011; 286(19):16743-50, 14 pgs.

Sumanas S, et al., "Zebrafish chaperone protein GP96 is required for otolith formation during ear development," Developmental Biology, 2003; 261(2):443-55, 13 pgs.

Sumanas S, et al., "Morpholino phosphorodiamidate oligonucleotides in zebrafish: a recipe for functional genomics?" Briefings in Functional Genomics & Proteomics 2002; 1(3):239-56, 18 pgs.

Sumanas S, et al., "Ets1-related protein is a key regulator of vasculogenesis in zebrafish," PloS Biology, 2006; 4(1):e10, 10 pgs.

Sumanas S, et al., "15-zinc finger protein Bloody Fingers is required for zebrafish morphogenetic movements during neurulation," Developmental Biology 2005; 283(1):85-96, 12 pgs.

Syvänen, A.-C., "Accessing Genetic Variation: Genotyping Single Nucleotide Polymorphisms," Nature Reviews Genetics, Dec. 2001, 2:930-942, 13 pgs.

Takahashi H, et al., "Human mediator subunit MED26 functions as a docking site for transcription elongation factors," Cell, 2011; 146(1):92-104, 23 pgs.

Tsutsui T, et al., "Mediator complex recruits epigenetic regulators via its two cyclin-dependent kinase subunits to repress transcription of immune response genes," J Biol Chem, 2013; 288(29):20955-65, 12 pgs.

Tyrrell C, et al., "Isoleucine/leucine2 is essential for chemoattractant activity of beta-defensin Defb14 through chemokine receptor 6," Molecular Immunology, 2010; 47(6):1378-82, 5 pgs.

Vissers LE, et al., "A de novo paradigm for mental retardation," Nat Genet, 2010; 42(12):1109-12, 5 pgs.

Wongdee K, et al., "Osteoblasts express claudins and tight junction-associated proteins," Histochemistry and Cell Biology, 2008; 130(1):79-90, 12 pgs.

U.S. Appl. No. 61/978,614, filed Apr. 11, 2014.

\* cited by examiner

METHODS AND DEVICES FOR BONE INFECTION TREATMENT SELECTION

CROSS-REFERENCE TO RELATED APPLICATION

This application claims the benefit of and priority to U.S. patent application Ser. No. 14/681,673, filed Apr. 8, 2015, entitled "Methods and Devices for Bone Infection Treatment Selection," which claims the benefit of and priority to U.S. Provisional Patent Application Ser. No. 61/978,614, filed Apr. 11, 2014, entitled "Methods and Devices for Bone Infection Treatment Selection," the contents of which are incorporated herein in their entirety for all purposes.

BACKGROUND

Osteomyelitis is the second most common invasive childhood infection that requires hospitalization; nevertheless, its pathogenesis is poorly understood. *Staphylococcus aureus* is an ever-present pathogen for both children and adults. Although skin and soft tissue infections are the most common reason for treatment, invasive disease due to *S. aureus* is also on the rise: sepsis, pneumonia, osteomyelitis, septic arthritis, brain abscess. Osteomyelitis accounts for a substantial number of cases of invasive *S. aureus* disease. Osteomyelitis is thought to occur when *S. aureus* or other bacteria enter the skin, invade the bloodstream, and are carried to the metaphysis of a long bone. Most children present with infection in a single bone and improve quickly with 7-10 days of intravenous antibiotics and another 2-3 weeks of oral therapy. Despite encompassing knowledge of the organism and its virulence factors, very little is known about host susceptibility to *S. aureus*.

As such, there is a need for compositions and methods for detection of individuals susceptible to *S. aureus*, such that appropriate treatment may be administered. The instant disclosure seeks to address one or more of these needs in the art.

SUMMARY

Disclosed are methods for identifying patients at increased risk of developing disseminated staphylococcal infection, which includes the steps of determining that the patient has a mutation in one or more genes selected from a MPDZ network gene, a CGNL1 network gene, a PRKRIR network gene, a MED26 network gene, a tight junction protein gene, or an immune modulator gene, or combinations thereof; and treating the patient for disseminated staphylococcal infection. Also disclosed are solid substrates and/or assays useful for carrying out the disclosed methods.

DETAILED DESCRIPTION

Disclosed herein are methods and compositions for the stratification of patients having bone infection, wherein patients having a need for surgical intervention and/or specific antibiotics (e.g., bacteriocidal antibiotics) are identified.

The term "biomarker" as used herein refers to a gene that comprises one or more mutations as compared to the wild type gene and is predictive of different disease prognosis, survival outcome, or preferred methods of treatment.

The term "nucleic acid" includes DNA and RNA and can be either double stranded or single stranded.

The term "hybridize" or "hybridizable" refers to the sequence specific non-covalent binding interaction with a complementary nucleic acid. Hybridization may be under high stringency conditions. Appropriate stringency conditions which promote hybridization will be understood to those skilled in the art.

The term "probe" as used herein refers to a nucleic acid sequence that will hybridize to a nucleic acid target sequence (e.g., a biomarker). In one example, the probe hybridizes to an RNA product of the biomarker or a nucleic acid sequence complementary thereof. The length of probe depends on the hybridization conditions and the sequences of the probe and nucleic acid target sequence. In one embodiment, the probe may be at least 8, 10, 15, 20, 25, 50, 75, 100, 150, 200, 250, 400, 500 or more nucleotides in length.

A "region" of a probe or biomarker, as used herein, may comprise or consist of 8, 9, 10, 11, 12, 13, 14, 15, 16, 17, 18, 19, 20, 21, 22, 23, 24, 25, 26, 27, 28, 29 or more contiguous nucleotides from a particular gene or a complementary sequence thereof. In some embodiments, the region may be of the same length as the probe or the biomarker. In other embodiments, the region may be shorter than the length of the probe or the biomarker.

The term "subject" as used herein refers to any member of the animal kingdom.

The term "target specific probe" encompasses probes that have a region of contiguous nucleotides having a sequence that is either (i) identically present in one of the disclosed genes, or (ii) complementary to the sequence of a region of contiguous nucleotides found in one of the disclosed genes, where "region" can comprise the full length sequence of any one of the disclosed genes, a complementary sequence of the full length sequence of any one of the disclosed genes, or a subsequence thereof.

Applicant has identified mutations in certain genes that may operate as biomarkers that can be used to screen subjects with osteomyelitis, in particular children, immediately upon diagnosis. The biomarkers may be used in conjunction with a solid surface array as is known in the art. Those subjects with mutations in the certain genes (the biomarkers) may then be considered at risk for disseminated staphylococcal infection after osteomyelitis and would receive bactericidal antibiotics with surgical extirpation of the site of infection in bone. A solid surface array or other screening device, as described herein or as otherwise appreciated in the art, may be used as a risk-stratification tool to predict which subjects with osteomyelitis have an underlying genetic susceptibility for disseminated staphylococcal infection as a consequence of osteomyelitis, such that they may be quickly treated using the most effective therapeutic protocol.

Method of Treatment

In one aspect, a method of treatment is disclosed. The method may comprise the steps of a) identifying a patient having a bone infection; b) determining that the patient has a mutation in one or more genes selected from a MPDZ network gene, a CGNL1 network gene, a PRKRIR network gene, a MED26 network gene, a tight junction protein gene, an immune modulator gene, and combinations thereof; and c) treating the patient for disseminated staphylococcal infection.

In one aspect, the bone infection may be osteomyelitis.

In one aspect, the treatment step may comprise surgical intervention, treatment with a bacteriocidal antibiotic, or a combination thereof.

In one aspect, the treatment step may comprise surgical intervention, treatment with a bactericidal antibiotic for *staphylococcus aureus*, or a combination thereof.

In one aspect, the antibiotic used in the treatment step may be selected from teicoplanin, vancomycin, gentamicin, and combinations thereof. In one aspect, the antibiotic may comprise vancomycin.

In one aspect, the gene may be selected from MPDZ, CLDN1, CLDN4, CLDN5, CLDN8, TLN2, KCNJ15, SYNGP1, PLEKHA2, AMOT, CGNL1, CGN, TMOD3, TMOD2, DMXL2, TLN2, MPAK6, DOK4, CDH5, GATA4, GEF-H1, TIAM1, PRKRIR, STK4, DNAJC3, EIF2AK2, EIF2S1, DDX58, TP53, UBC, MED1,4, MED6,7,8,9, MED10, 11, 12, MED 13, 14, 15, MED 17, 18, 19, MED20, 21, 23, MED25, 26, 27, 28, MED 29, 30, 31, SREBF1, TRRAP, CTDP1, TADA2A, CDK8, 19, ZO1,2,3, CTNNA1, 2, 3, CTNNB1, MARVELD2, 3, OCLN, JAM2, 3, ESAM, CYBA, CYBB, NCF2, CEBPE, STAT1, IL1R1, TNFSF11, IL12RB1, IFNGR1/2, and combinations thereof (See Table 1).

TABLE 1

| MPDZ network (10) | CGNL1 network (12) | PRKRIR network (8) | MED26 Network (31) | Tight junction proteins (13) | Immune modulators (9) |
| --- | --- | --- | --- | --- | --- |
| MPDZ | CGNL1 | PRKRIR | MED1, 4 | ZO1, 2, 3 | CYBA |
| CLDN1 | CGN | STK4 | MED6, 7, 8, 9 | CTNNA1, 2, 3 | CYBB |
| CLDN4 | TMOD3 | DNAJC3 | MED10, 11, 12 | CTNNB1 | NCF2 |
| CLDN5 | TMOD2 | EIF2AK2 | MED13, 14, 15 | MARVELD2, 3 | CEBPE |
| CLDN8 | DMXL2 | EIF2S1 | MED17, 18, 19 | OCLN | STAT1 |
| TLN2 | TLN2 | DDX58 | MED20, 21, 23 | JAM2, 3 | IL1R1 |
| KCNJ15 | MPAK6 | TP53 | MED25, 26, 27, 28 | ESAM | TNFSF11 |
| SYNGAP1 | DOK4 | UBC | MED29, 30, 31 | | IL12RB1 |
| PLEKHA2 | CDH5 | | SREBF1 | | IFNGR1/2 |
| AMOT | GATA4 | | TRRAP | | |
| | GEF-H1 | | CTDP1 | | |
| | TIAM1 | | TADA2A | | |
| | | | CDK8, 19 | | |

TABLE 2

Genes and representative, non-exhaustive, accession numbers.

| MPDZ | NM_003829.4 | MED17 | NM_004268.4 |
| --- | --- | --- | --- |
| CLDN1 | NM_021101.4 | MED18 | NM_017638.2 |
| CLDN4 | NM_001305.4 | MED19 | NM_153450.1 |
| CLDN5 | NM_001130861.1 | MED20 | NM_004275.3 |
| CLDN8 | NM_199328.2 | MED21 | NM_004264.4 |
| TLN2 | NM_015059.2 | MED23 | NM_004830.3 |
| SYNGAP1 | NM_006772.2 | MED25 | NM_030973.3 |
| PLEKHA2 | NM_021623.1 | MED26 | NM_004831.3 |
| AMOT | NM_001113490.1 | MED27 | NM_004269.3 |
| KCNJ15 | NM_170736.2 | MED28 | NM_025205.3 |
| CGNL1 | NM_001252335.1 | MED29 | NM_017592.1 |
| CGN | NM_020770.2 | MED30 | NM_080651.3 |
| TMOD3 | NM_014547.4 | MED31 | NM_016060.2 |
| TMOD2 | NM_014548.3 | SREBF1 | NM_001005291.2 |
| DMXL2 | NM_001174116.1 | TRRAP | NM_001244580.1 |
| MPAK6 | | CTDP1 | NM_004715.4 |
| DOK4 | NM_018110.3 | TADA2A | NM_001488.3 |
| CDH5 | NM_001795.3 | CDK8 | NM_001260.1 |
| GATA4 | NM_002052.3 | CDK19 | NM_015076.3 |
| GEF-H1 | NM_001162383 | ZO1 | |
| TIAM1 | NM_003253.2 | ZO2 | |

TABLE 2-continued

Genes and representative, non-exhaustive, accession numbers.

| PRKRIR | NM_004705.2 | ZO3 | |
| --- | --- | --- | --- |
| STK4 | NM_006282.2 | CTNNA1 | NM_001903.3 |
| DNAJC3 | NM_006260.4 | CTNNA2 | NM_004389.3 |
| EIF2AK2 | NM_001135652.2 | CTNNA3 | NM_013266.3 |
| EIF2S1 | NM_004094.4 | CTNNB1 | NM_001904.3 |
| DDX58 | NM_014314.3 | MARVELD2 | NM_001038603.2 |
| TP53 | M_000546.5 | MARVELD3 | NM_001017967.3 |
| UBC | NM_021009.6 | OCLN | NM_002538.3 |
| MED1 | NM_004774.3 | JAM2 | NM_021219.3 |
| MED4 | NM_014166.3 | JAM3 | NM_032801.4 |
| MED6 | NM_001284209.1 | ESAM | NM_138961.2 |
| MED7 | NM_001100816.1 | CYBA | NM_000101.3 |
| MED8 | NM_001001653.2 | CYBB | NM_000397.3 |
| MED9 | NM_018019.2 | NCF2 | NM_000433.3 |
| MED10 | NM_032286.2 | CEBPE | NM_001805.3 |
| MED11 | NM_001001683.2 | STAT1 | NM_007315.3 |
| MED12 | NM_005120.2 | IL1R1 | NM_000877.3 |
| MED15 | NM_001003891.1 | TNFSF11 | NM_003701.3 |
| MED14 | NM_004229.3 | IL12RB1 | NM_005535.2 |
| MED13 | NM_005121.2 | IFNGR1 | NM_000416.2 |
| | | IFNGR2 | NM_005534.3 |

The above list of accession numbers is intended to be for reference only, and is not intended to limit the scope of the invention. The full sequence as listed in the accession database for the above-referenced numbers is incorporated herein by reference. It is understood that variants of the disclosed genes are within the scope of the invention, as would be understood by one of ordinary skill in the art.

In one aspect, the mutation may be selected from a mutation in a PDZ domain of MPDZ, a mutation in an L27-2 domain of MPDZ, a Leu35Pro mutation in MPDZ, a mutation in a rod domain of CGNL1, a Leu to Ile mutation in CGNL1, a Leu739Ile mutation in CGNL1, a mutation in a nuclear export domain of PRKRIR, a Leu602Phe mutation of PRKRIR, a mutation in a TFIIS domain of MED26, an Ala464Thr mutation in MED26, or combinations thereof.

Arrays

In one aspect, an article for detecting one or more mutations in a gene sequence comprising a) a solid support; and b) one or more probes for assessing the presence or absence of a mutation in a gene sequence, wherein said gene may be selected from a MPDZ network gene, a CGNL1 network gene, a PRKRIR network gene, a MED26 network gene, a tight junction protein gene, an immune modulator gene, and combinations thereof; wherein said one or more probes may be affixed to said solid support; and wherein said one or more probes overlaps a region comprising said mutation in a gene sequence.

In one aspect, the MPDZ network may comprise MPDZ, CLDN1, CLDN4, CLDN5, CLDN8, TLN2, KCNJ15, SYNGP1, PLEKHA2, AMOT, and combinations thereof.

In one aspect, the CGNL1 network may comprise CGNL1, CGN, TMOD3, TMOD2, DMXL2, TLN2, MPAK6, DOK4, CDH5, GATA4, GEF-H1, TIAM1, and combinations thereof.

In one aspect, the PRKRIR network may comprise PRKRIR, STK4, DNAJC3, EIF2AK2, EIF2S1, DDX58, TP53, UBC, and combinations thereof.

In one aspect, the MED26 network may comprise MED1, 4, MED6,7,8,9, MED10, 11, 12, MED 13, 14, 15, MED 17, 18, 19, MED20, 21, 23, MED25, 26, 27, 28, MED 29, 30, 31, SREBF1, TRRAP, CTDP1, TADA2A, CDK8, 19, and combinations thereof.

In one aspect, the one or more sequences encoding a tight junction protein may comprise ZO1,2,3, CTNNA1, 2, 3, CTNNB1, MARVELD2, 3, OCLN, JAM2, 3, ESAM, and combinations thereof.

In one aspect, the one or more sequences encoding an immune modulator may comprise CYBA, CYBB, NCF2, CEBPE, STAT1, IL1R1, TNFSF11, IL12RB1, IFNGR1/2, and combinations thereof.

In one aspect, the solid support may comprise the MPDZ sequence.

In one aspect, the solid support may comprise the MPDZ sequence, wherein said MPDZ sequence may comprise a mutation in a PDZ domain.

In one aspect, the solid support may comprise the MPDZ sequence, wherein said MPDZ sequence may comprise a mutation in an L27-2 domain.

In one aspect, the solid support may comprise the MPDZ sequence, wherein said sequence may comprise a Leu35Pro mutation.

In one aspect, the solid support may comprise the CGNL1 sequence.

In one aspect, the solid support may comprise the CGNL1 sequence, wherein said CGNL1 sequence may comprise a mutation in a rod domain.

In one aspect, the solid support may comprise the CGNL1 sequence, wherein said CGNL1 sequence may comprise a Leu to Ile mutation.

In one aspect, the solid support may comprise the CGNL1 sequence, wherein said CGNL1 sequence may comprise a Leu739Ile mutation.

In one aspect, the solid support may comprise the PRKRIR sequence.

In one aspect, the solid support may comprise the PRKRIR sequence, wherein said PRKRIR sequence may comprise a mutation in a nuclear export domain.

In one aspect, the solid support may comprise the PRKRIR sequence, wherein said PRKRIR sequence may comprise a Leu602Phe mutation.

In one aspect, the solid support may comprise the MED26 sequence.

In one aspect, the solid support may comprise the MED26 sequence, wherein said MED26 sequence may comprise a mutation in a TFIIS domain.

In one aspect, the solid support may comprise the MED26 sequence, wherein said MED26 sequence may comprise an Ala464Thr mutation.

A person skilled in the art will appreciate that a number of methods can be used to detect a mutation in a sample, including arrays, such as microarrays, RT-PCR, nuclease protection assays, multiplex assays including nanostring technology, and Northern blot analyses. Any analytical procedure capable of permitting specific and quantifiable (or semi-quantifiable) detection of the biomarkers may be used in the disclosed methods, such as the microarray and quantitative PCR, e.g. quantitative RT-PCR, methods set forth herein, and methods known to those skilled in the art.

Accordingly, in one aspect, the mutation may be determined using arrays, optionally microarrays, RT-PCR, optionally quantitative RT-PCR, nuclease protection assays or Northern blot analyses.

In some aspects, the mutation may be determined by using an array. cDNA microarrays may consist of multiple (usually thousands) of different cDNA probes spotted (usually using a robotic spotting device) onto known locations on a solid support, such as a glass microscope slide. Such arrays are well known in the art. Microarrays for use in the methods described herein may comprise a solid substrate onto which the probes are covalently or non-covalently attached. The cDNAs are typically obtained by PCR amplification of plasmid library inserts using primers complementary to the vector backbone portion of the plasmid or to the gene itself for genes where sequence is known. PCR products suitable for production of microarrays are typically between 0.5 and 2.5 kB in length. In a typical microarray experiment, RNA (either total RNA or poly A RNA) may be isolated from cells or tissues of interest and is reverse transcribed to yield cDNA. Labeling is usually performed during reverse transcription by incorporating a labeled nucleotide in the reaction mixture. A microarray may then be hybridized with labeled RNA. Microarray analysis can be performed by commercially available equipment, following manufacturer's protocols, such as by using Affymetrix GeneChip technology, Agilent Technologies cDNA microarrays, Illumina Whole-Genome DASL array assays, or any other comparable microarray technology.

In some aspects, probes capable of hybridizing to one or more RNAs or cDNAs may be attached to a substrate at a defined location ("addressable array"). Probes can be attached to the substrate in a wide variety of ways, as will be appreciated by those in the art. In some embodiments, the probes are synthesized first and subsequently attached to the substrate. In other embodiments, the probes are synthesized on the substrate. In some aspects, probes may be synthesized on the substrate surface using techniques such as photopolymerization and photolithography.

In some aspects, microarrays may be utilized in a RNA-primed, Array-based Klenow Enzyme ("RAKE") assay. See Nelson, P. T. et al. (2004) Nature Methods 1(2):1-7; Nelson, P. T. et al. (2006) RNA 12(2):1-5. In these embodiments, total RNA may be isolated from a sample. Optionally, small RNAs can be further purified from the total RNA sample. The RNA sample is then hybridized to DNA probes immobilized at the 5'-end on an addressable array. The DNA probes may comprise a base sequence that is complementary to a target RNA of interest, such as one or more RNAs capable of specifically hybridizing to a nucleic acid comprising a sequence identified herein.

In some aspects, the array may comprise DNA probes for no more than the genes disclosed herein. In other aspects, the array may comprise additional DNA probes.

In one aspect, after the sample is hybridized to the array, the sample may be exposed to exonuclease I to digest any unhybridized probes. The Klenow fragment of DNA polymerase I may then be applied along with biotinylated dATP, allowing the hybridized biomarker to act as primers for the enzyme with the DNA probe as template. The slide may then be washed and a streptavidin-conjugated fluorophore may be applied to detect and quantify the spots on the array containing hybridized and Klenow-extended biomarker RNAs from the sample.

In some embodiments, an RNA sample may be reverse transcribed using a biotin/poly-dA random octamer primer. The RNA template may be digested and the biotin-containing cDNA may be hybridized to an microarray with bound probes that permit specific detection of biomarker RNAs. The microarray may include at least one probe comprising at least 8, at least 9, at least 10, at least 11, at least 12, at least 13, at least 14, at least 15, at least 16, at least 17, at least 18, at least 19, even at least 20, 21, 22, 23, or 24 contiguous nucleotides identically present in each of the genes disclosed herein. After hybridization of the cDNA to the microarray, the microarray may then be exposed to a streptavidin-bound detectable marker, such as a fluorescent dye, and the bound cDNA is detected, as is known in the art.

In some aspects, compositions are provided that comprise at least one target specific probe.

In some aspects, target specific probes may consist of deoxyribonucleotides. In other aspects, target specific probes may consist of both deoxyribonucleotides and nucleotide analogs. In some aspects, biomarker RNA-specific probes comprise at least one nucleotide analog which may increase the hybridization binding energy.

In some aspects, a target specific probe in the compositions described herein binds to one biomarker RNA or DNA in the sample.

In some aspects, more than one probe specific for a single biomarker sequence may be present in the compositions, the probes capable of binding to overlapping or spatially separated regions of the biomarker sequence.

It will be understood that in some embodiments in which the compositions described herein are designed to hybridize to cDNAs reverse transcribed from biomarker RNAs, the composition may comprise at least one target specific probe comprising a sequence that is identically present in a biomarker RNA (or a subsequence thereof).

In some aspects, a biomarker sequence may be capable of specifically hybridizing to at least one probe comprising a base sequence that is identically present in one of the genes disclosed herein. In some aspects, a biomarker sequence may be capable of specifically hybridizing to at least one nucleic acid probe comprising a sequence that is identically present in one of the genes disclosed herein.

In some aspects, the composition may comprise a plurality of target or biomarker sequence specific probes each comprising a region of contiguous nucleotides comprising a base sequence that is identically present in one or more of the disclosed genes, or in a subsequence of a disclosed gene. In some aspects, the composition may comprise a plurality of target or biomarker sequence specific probes each comprising a region of contiguous nucleotides comprising a base sequence that is complementary to a sequence of a disclosed gene.

In some aspects, the microarray may comprise probes comprising a region with a base sequence that is fully complementary to a target region of a biomarker. In other aspects, the microarray may comprise probes comprising a region with a base sequence that may comprise one or more base mismatches when compared to the sequence of the best-aligned target region of a biomarker.

In some aspects, the microarray may comprise may comprise probes each comprising a region of at least 10 contiguous nucleotides, such as at least 11 contiguous nucleotides, such as at least 13 contiguous nucleotides, such as at least 14 contiguous nucleotides, such as at least 15 contiguous nucleotides, such as at least 16 contiguous nucleotides, such as at least 17 contiguous nucleotides, such as at least 18 contiguous nucleotides, such as at least 19 contiguous nucleotides, such as at least 20 contiguous nucleotides, such as at least 21 contiguous nucleotides, such as at least 22 contiguous nucleotides, such as at least 23 contiguous nucleotides, such as at least 24 contiguous nucleotides, such as at least 25 contiguous nucleotides with a base sequence that is identically present in one of the disclosed genes, or a variant thereof.

In some aspects, the microarray component may comprise probes each comprising a region with a base sequence that is identically present in each of the disclosed genes, or a variant thereof.

In some aspects, the analytical method used for detecting at least one biomarker may include real-time quantitative RT-PCR. Although PCR can use a variety of thermostable DNA-dependent DNA polymerases, it typically employs the Taq DNA polymerase, which has a 5'-3' nuclease activity but lacks a 3'-5' proofreading endonuclease activity. In some aspects, RT-PCR is done using a TaqMan® assay sold by Applied Biosystems, Inc. RT-PCR may be performed using any RT-PCR instrumentation available in the art. Instrumentation used in real-time RT-PCR data collection and analysis may comprise a thermal cycler, optics for fluorescence excitation and emission collection, and optionally a computer and data acquisition and analysis software.

In various other aspects, RT-PCR detection may be utilized to detect, in a single multiplex reaction, one or more biomarkers. The biomarkers, in some aspects, may be capable of specifically hybridizing to a nucleic acid comprising a sequence that is identically present in one of the disclosed genes.

In some aspects, a plurality of probes, such as TaqMan probes, each specific for a different target sequence, may be used. Each target-specific probe may be spectrally distinguishable from the other probes used in the same multiplex reaction.

In some aspects, the methods of detecting at least one biomarker described herein may employ one or more modified oligonucleotides, such as oligonucleotides comprising one or more affinity-enhancing nucleotides. Modified oligonucleotides useful may include primers for reverse transcription, PCR amplification primers, and probes. In some aspects, the incorporation of affinity-enhancing nucleotides may increases the binding affinity and specificity of an oligonucleotide for its target nucleic acid as compared to oligonucleotides that contain only deoxyribonucleotides, and allows for the use of shorter oligonucleotides or for shorter regions of complementarity between the oligonucleotide and the target nucleic acid. Affinity-enhancing nucleotides may include nucleotides comprising one or more base modifications, sugar modifications and/or backbone modifications. Modified bases for use in affinity-enhancing nucleotides may include 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine. Affinity-enhancing modifications may include nucleotides having modified sugars such as 2'-substituted sugars, such as 2'-O-alkyl-ribose sugars, 2'-amino-deoxyribose sugars, 2'-fluoro-deoxyribose sugars, 2'-fluoro-arabinose sugars, and 2'-O-methoxyethyl-ribose (2'MOE) sugars. In some aspects, modified sugars are arabinose sugars, or d-arabino-hexitol sugars. Affinity-enhancing modifications may also include backbone modifications such as the use of peptide nucleic acids (e.g., an oligomer including nucleobases linked together by an amino acid backbone). Other backbone modifications include phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

In some aspects, the oligomer may include at least one affinity-enhancing nucleotide that has a modified base, at least nucleotide (which may be the same nucleotide) that has a modified sugar, and at least one internucleotide linkage that is non-naturally occurring. In some aspects, the affinity-enhancing nucleotide may contain a locked nucleic acid ("LNA") sugar, which is a bicyclic sugar. In some aspects, an oligonucleotide for use in the methods described herein may comprise one or more nucleotides having an LNA sugar. In some aspects, the oligonucleotide contains one or more regions consisting of nucleotides with LNA sugars. In other aspects, the oligonucleotide contains nucleotides with LNA sugars interspersed with deoxyribonucleotides. See, e.g., Frieden, M. et al. (2008) Curr. Pharm. Des. 14(11): 1138-1142.

REFERENCES

1. Ardura M I, Banchereau R, Mejias A, Di Pucchio T, Glaser C, Allantaz F, Pascual V, Banchereau J, Chaussabel D, Ramilo O. Enhanced monocyte response and decreased central memory T cells in children with invasive *Staphylococcus aureus* infections. PLoS One 2009; 4(5):e5446. PMCID: 2676512.
2. Holland S M, DeLeo F R, Elloumi H Z, Hsu A P, Uzel G, Brodsky N, Freeman A F, Demidowich A, Davis J, Turner M L, Anderson V L, Darnell D N, Welch P A, Kuhns D B, Frucht D M, Malech H L, Gallin J I, Kobayashi S D, Whitney A R, Voyich J M, Musser J M, Woellner C, Schaffer A A, Puck J M, Grimbacher B. STAT3 mutations in the hyper-IgE syndrome. N Engl J Med 2007; 357(16): 1608-19.
3. Ku C L, Picard C, Erdos M, Jeurissen A, Bustamante J, Puel A, von Bernuth H, Filipe-Santos O, Chang H H, Lawrence T, Raes M, Marodi L, Bossuyt X, Casanova J L. IRAK4 and NEMO mutations in otherwise healthy children with recurrent invasive pneumococcal disease. J Med Genet 2007; 44(1):16-23. PMCID: 2597905.
4. Dinauer M C. Chronic granulomatous disease and other disorders of phagocyte function. Hematology Am Soc Hematol Educ Program 2005:89-95.
5. Vissers L E, de Ligt J, Gilissen C, Janssen I, Steehouwer M, de Vries P, van Lier B, Arts P, Wieskamp N, del Rosario M, van Bon B W, Hoischen A, de Vries B B, Brunner H G, Veltman J A. A de novo paradigm for mental retardation. Nat Genet 2010; 42(12):1109-12.
6. Le Saux N, Howard A, Barrowman N J, Gaboury I, Sampson M, Moher D. Shorter courses of parenteral antibiotic therapy do not appear to influence response rates for children with acute hematogenous osteomyelitis: a systematic review. BMC infectious diseases 2002; 2:16. PMCID: 128824.
7. Pulimeno P, Paschoud S, Citi S. A role for ZO-1 and PLEKHA7 in recruiting paracingulin to tight and adherens junctions of epithelial cells. J Biol Chem 2011; 286(19):16743-50. PMCID: 3089516.
8. Paschoud S, Yu D, Pulimeno P, Jond L, Turner J R, Citi S. Cingulin and paracingulin show similar dynamic behaviour, but are recruited independently to junctions. Molecular membrane biology 2011; 28(2):123-35.
9. Wongdee K, Pandaranandaka J, Teerapornpuntakit J, Tudpor K, Thongbunchoo J, Thongon N, Jantarajit W, Krishnamra N, Charoenphandhu N. Osteoblasts express claudins and tight junction-associated proteins. Histochemistry and cell biology 2008; 130(1):79-90.
10. Guillemot L, Paschoud S, Jond L, Foglia A, Citi S. Paracingulin regulates the activity of Rac1 and RhoA GTPases by recruiting Tiam1 and GEF-H1 to epithelial junctions. Molecular biology of the cell 2008; 19(10): 4442-53. PMCID: 2555940.
11. Paschoud S, Guillemot L, Citi S. Distinct domains of paracingulin are involved in its targeting to the actin cytoskeleton and regulation of apical junction assembly. J Biol Chem 2012; 287(16):13159-69. PMCID: 3340007.
12. Prodromou C, Nuttall J M, Millson S H, Roe S M, Sim T S, Tan D, Workman P, Pearl L H, Piper P W. Structural basis of the radicicol resistance displayed by a fungal hsp90. ACS chemical biology 2009; 4(4):289-97.
13. Tyrrell C, De Cecco M, Reynolds N L, Kilanowski F, Campopiano D, Barran P, Macmillan D, Dorin J R. Isoleucine/leucine2 is essential for chemoattractant activity of beta-defensin Defb14 through chemokine receptor 6. Molecular immunology 2010; 47(6):1378-82.
14. Takahashi H, Parmely T J, Sato S, Tomomori-Sato C, Banks C A, Kong S E, Szutorisz H, Swanson S K, Martin-Brown S, Washburn M P, Florens L, Seidel C W, Lin C, Smith E R, Shilatifard A, Conaway R C, Conaway J W. Human mediator subunit MED26 functions as a docking site for transcription elongation factors. Cell 2011; 146(1):92-104. PMCID: 3145325.
15. Tsutsui T, Fukasawa R, Shinmyouzu K, Nakagawa R, Tobe K, Tanaka A, Ohkuma Y. Mediator complex recruits epigenetic regulators via its two cyclin-dependent kinase subunits to repress transcription of immune response genes. J Biol Chem 2013; 288(29):20955-65. PMCID: 3774365.
16. Hoskins E E, Morris T A, Higginbotham J M, Spardy N, Cha E, Kelly P, Williams D A, Wikenheiser-Brokamp K A, Duensing S, Wells S I. Fanconi anemia deficiency stimulates HPV-associated hyperplastic growth in organotypic epithelial raft culture. Oncogene 2009; 28(5):674-85. PMCID: 2636855.
17. Lanaspa M A, Almeida N E, Andres-Hernando A, Rivard C J, Capasso J M, Berl T. The tight junction protein, MUPP1, is up-regulated by hypertonicity and is important in the osmotic stress response in kidney cells. Proceedings of the National Academy of Sciences of the United States of America 2007; 104(34):13672-7. PMCID: 1959440.
18. Ohnishi H, Nakahara T, Furuse K, Sasaki H, Tsukita S, Furuse M. JACOP, a novel plaque protein localizing at the apical junctional complex with sequence similarity to cingulin. J Biol Chem 2004; 279(44):46014-22.
19. Becamel C, Figge A, Poliak S, Dumuis A, Peles E, Bockaert J, Lubbert H, Ullmer C. Interaction of serotonin 5-hydroxytryptamine type 2C receptors with PDZ10 of the multi-PDZ domain protein MUPP1. J Biol Chem 2001; 276(16):12974-82.
20. Frank C F, Hostetter M K. Cleavage of E-cadherin: a mechanism for disruption of the intestinal epithelial barrier by *Candida albicans*. Translational research: the journal of laboratory and clinical medicine 2007; 149(4): 211-22.
21. Bill B R, Petzold A M, Clark K J, Schimmenti L A, Ekker S C. A primer for morpholino use in zebrafish. Zebrafish 2009; 6(1):69-77. PMCID: 2776066.
22. Sumanas S, Larson J D. Morpholino phosphorodiamidate oligonucleotides in zebrafish: a recipe for functional genomics? Briefings in functional genomics & proteomics 2002; 1(3):239-56.
23. Sumanas S, Larson J D, Miller Bever M. Zebrafish chaperone protein GP96 is required for otolith formation during ear development. Developmental biology 2003; 261(2):443-55.
24. Sumanas S, Lin S. Ets1-related protein is a key regulator of vasculogenesis in zebrafish. PLoS biology 2006; 4(1): e10. PMCID: 1310653.
25. Sumanas S, Zhang B, Dai R, Lin S. 15-zinc finger protein Bloody Fingers is required for zebrafish morphogenetic movements during neurulation. Developmental biology 2005; 283(1):85-96.
26. Kwong R W, Perry S F. The tight junction protein claudin-b regulates epithelial permeability and sodium handling in larval zebrafish, Danio rerio. American journal of physiology Regulatory, integrative and comparative physiology 2013; 304(7):R504-13. PMCID: 3627946.

27. Collins M M, Baumholtz A I, Ryan A K. Claudin-5 expression in the vasculature of the developing chick embryo. Gene expression patterns: GEP 2012.
28. Furuse M, Moriwaki K. The role of claudin-based tight junctions in morphogenesis. Annals of the New York Academy of Sciences 2009; 1165:58-61.
29. Gordon D L, Johnson G M, Hostetter M K. Ligand-receptor interactions in the phagocytosis of virulent *Streptococcus pneumoniae* by polymorphonuclear leukocytes. J Infect Dis 1986; 154(4):619-26.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A method of detecting a mutation in a human diagnosed with a bone infection, said method comprising
   detecting the presence of a Leu35Pro mutation in MPDZ in a biological sample obtained from said human with a probe specific for the Leu35Pro mutation in MPDZ; wherein said detecting step is carried out by detecting binding between said probe and said Leu35Pro mutation in MPDZ.

2. The method of claim 1, further comprising the step of detecting whether a Leu602Phe mutation in PRKRIR is present using a nucleic acid probe specific to said Leu602Phe mutation and comprising a detectable label.

3. The method of claim 1, further comprising the step of detecting whether a Leu739Ile mutation in CGNL1 is present using a nucleic acid probe specific to said Leu739Ile mutation and comprising a detectable label.

4. The method of claim 1, further comprising the step of detecting whether an Ala464Thr mutation in MED26 is present using a nucleic acid probe specific to said Ala464Thr mutation and comprising a detectable label.

5. The method of claim 1, wherein said probe comprises a detectable label.

* * * * *